United States Patent
Meier et al.

[11] Patent Number: 5,596,099
[45] Date of Patent: *Jan. 21, 1997

[54] PROCESS FOR THE PREPARATION OF N-(2-SULFATOETHYL)-PIPERAZINE IN HIGH PURITY

[75] Inventors: Michael Meier, Frankfurt am Main; Heinz-Georg Kautz, Birstein, both of Germany

[73] Assignee: Hoechst Aktiengesellschaft, Germany

[*] Notice: The portion of the term of this patent subsequent to Mar. 15, 2015, has been disclaimed.

[21] Appl. No.: 405,381

[22] Filed: Mar. 15, 1995

Related U.S. Application Data

[63] Continuation of Ser. No. 154,267, Nov. 18, 1993, abandoned.

[30] Foreign Application Priority Data

Nov. 21, 1992 [DE] Germany .......................... 42 39 183.0

[51] Int. Cl.$^6$ ............................................. C07D 295/088
[52] U.S. Cl. ............................................................ 544/398
[58] Field of Search ................................................. 544/398

[56] References Cited

U.S. PATENT DOCUMENTS 3,194,822   7/1965   Goldstein ................................... 558/29

FOREIGN PATENT DOCUMENTS 238227   2/1960   Australia ................................ 558/29

OTHER PUBLICATIONS

*Organic Functional Group Preparations* by Stanley R. Sandler and Wolf Karo, vol. III p. 116–124 (1972).
*Research Techniques in Organic Chemistry* by Robert B. Bates, John P. Schaefer, pp. 50,51,55 (1971).
Tomalia et al, *J. Het. Chem.* 9, pp. 891–894 (1972).
Andrew Streitweiser, Jr., "Introduction to Organic Chemistry", Second Edition, p. 815 (1981).
Barton & Ollis, "Comprehensive Organic Chemistry", vol. 3, p. 370 (1979).

*Primary Examiner*—Emily Bernhardt
*Attorney, Agent, or Firm*—Connolly & Hutz

[57] ABSTRACT

A process for the preparation of N-(2-sulfatoethyl)-piperazine in high purity, which comprises reacting N-(2-hydroxyethyl)piperazine in a mixture of highly—or relatively highly—concentrated sulfuric acid and oleum or chlorosulfonic acid at temperatures of from about 80° to about 250° C., transferring the resulting sulfonation mixture to a water-miscible aliphatic alcohol, isolating the N-(2-sulfatoethyl)piperazine sulfate formed, treating the N-(2-sulfatoethyl)piperazine sulfate, still moist with alcohol, at temperatures of from about 35° to about 90° C. with a basic compound in a mixture of a ($C_1$–$C_2$)-alkanol and water, separating off the precipitated sulfate of the basic compound employed, and isolating the N-(2-sulfatoethyl)piperazine formed, by the addition of ($C_1$–$C_2$)-alkanol.

24 Claims, No Drawings

PROCESS FOR THE PREPARATION OF N-(2-SULFATOETHYL)-PIPERAZINE IN HIGH PURITY

This application is a continuation of U.S. application Ser. No. 08/154,267, filed Nov. 18, 1993, now abandoned.

DESCRIPTION

The invention relates to a process for the preparation of N-(2-sulfatoethyl)piperazine in high purity by reacting N-(2-hydroxyethyl)piperazine in a mixture of highly—or relatively highly—concentrated sulfuric acid and oleum or chlorosulfonic acid, transferring the resulting sulfonation mixture to a water-miscible aliphatic alcohol, isolating the N-(2-sulfatoethyl)piperazine sulfate formed, reacting the N-(2-sulfatoethyl)piperazine sulfate with a basic compound in a mixture of a $(C_1-C_2)$-alkanol and water, and separating off the precipitated sulfate of the basic compound employed.

N-(2-Sulfatoethyl)piperazine can be employed as an agent for the pretreatment and modification of fiber materials, such as synthetic polyamide or polyurethane fiber materials, wool, silk or cellulose fiber materials, for subsequent dyeing using anionic dyes (Patent Application P 41 40 410.6 which corresponds to U.S. patent application Ser. No. 07/984,977 which also corresponds to EP 546,476, which is incorporated by reference). EP 546 476 describes a process for the dyeing of fiber materials with watersoluble anionic dyes which using a fiber material pretreated and modified by the compounds containing ester and amino groups. As examples for compounds containing ester- and aminogroups are described: N-(β-Sulfatoethyl)piperazine, N-[β-(β'-sulfatoethoxy)-ethyl]-piperazine, N-(γ-sulfato-β-hydroxypropyl)-piperidine, 2,3-disulfato-1-aminopropane. For the preparation of these ester compounds the reaction of the corresponding hydroxyalkylamines with fuming sulfuric acid is described. The work-up procedure comprises the reaction with calcium carbonate, filtration of the formed calcium sulfate and precipitation of calcium ions which are still present with sodium oxalate. After filtration of the calcium oxalate the aqueous solution of the product is evaporated to dryness.

J. Heterocycl. Chem 9, 891–894 describes the possibility of obtaining N-(2-sulfatoethyl)piperazine in 70% yield as a viscous oil by reacting piperazine with ethylene sulfate in methylene chloride. On repetition of this process we did not succeed in preparing N-(2-sulfatoethyl)piperazine. Only a mixture of products was obtainable (cf. in this respect Example 4 below). Apart from this, the process described is disadvantageous in that the ethylene sulfate employed is not available as an industrial product.

There was therefore a need for an economic process, which is simple to carry out industrially, for the preparation of N-(2-sulfatoethyl)piperazine in high purity.

It has now been found, surprisingly, that N-(2-sulfatoethyl)piperazine can be prepared advantageously and in high purity by reacting N-(2-hydroxyethyl)piperazine in a mixture of highly—or relatively highly—concentrated sulfuric acid and oleum or chlorosulfonic acid at temperatures of from about 80° to about 250° C., preferably from about 100° to about 170° C., transferring the resulting sulfonation mixture to a water-miscible aliphatic alcohol, isolating the N-(2-sulfatoethyl)piperazine sulfate formed, treating the N-(2-sulfatoethyl)piperazine sulfate, still moist with alcohol, at temperatures of from about 35° to about 90° C., preferably from about 40 to about 70° C., with a basic compound in a mixture of a $(C_1-C_2)$-alkanol and water, separating off the precipitated sulfate of the basic compound employed, and isolating the N-(2-sulfatoethyl)piperazine formed, by the addition of $(C_1-C_2)$-alkanol.

In the process according to the invention, it is expedient to employ 100% strength sulfuric acid in a proportion of from about 0.8 to about 3 parts by weight, preferably from about 1.3 to about 1.7 parts by weight per part by weight of N-(2-hydroxyethyl)piperazine. Larger amounts of sulfuric acid can also be used. However, this leads to no qualitative advantages but only to the need to dispose of greater quantities of sulfuric acid. Instead of 100% strength sulfuric acid, it is also possible to employ a sulfuric acid of lower concentration, for example from 95 to 99% strength sulfuric acid, such as 96% strength sulfuric acid. In such cases it is necessary to use an additional amount, corresponding to the amount of water additionally present, of sulfur trioxide (in oleum) or chlorosulfonic acid.

When using a mixture of 100% strength sulfuric acid and oleum (a solution of sulfur trioxide in 100% strength sulfuric acid), sulfur trioxide is employed in a proportion of from about 0.3 to about 0.8 part by weight, preferably from about 0.4 to about 0.7 part by weight and particularly preferably from about 0.55 to about 0.65 part by weight per part by weight of N-(2-hydroxyethyl)piperazine. When using a mixture of relatively highly concentrated sulfuric acid and chlorosulfonic acid, the chlorosulfonic acid is employed in a proportion of from about 0.6 to about 1.3 parts by weight, preferably from about 0.7 to about 1.0 part by weight and particularly preferably from about 0.80 to about 0.95 part by weight per part by weight of N-(2-hydroxyethyl)piperazine.

The $(C_1-C_2)$-alkanol(s) employed is/are methanol and/or ethanol.

The proportion of the aqueous methanol or ethanol which is preferably used for the precipitation of the N-(2-sulfatoethyl)piperazine sulfate is from about 2.0 to about 6.0 parts by weight, preferably from about 3.0 to about 5.0 parts by weight and particularly preferably from about 3.2 to about 3.8 parts by weight per part by weight of N-(2-hydroxyethyl)piperazine. The water content of the alcohol should be between about 10 and about 30% by weight, preferably between about 15 and about 25% by weight. Precipitation is commenced at a temperature of about 45° C. and is then concluded by cooling to from about 15° to about 25° C. for complete crystallization. To achieve crystallization, from about 0.005 to about 10 parts by weight, preferably from about 0.01 to about 5 parts by weight and particularly preferably from about 0.05 to about 1 part by weight of N-(2-sulfatoethyl)piperazine sulfate per 130 parts by weight of N-(2-hydroxyethyl)piperazine are added to the precipitation mixture. It is, however, also possible to add greater quantities of seed crystals.

For purposes of further reaction (conversion of the N-(2-sulfatoethyl)piperazine sulfate to the highly pure N-(2-sulfatoethyl)piperazine), the N-(2-sulfatoethyl)piperazine sulfate can be employed still moist with alcohol, i.e. without being dried in between.

In this context it is expedient to transfer the N-(2-sulfatoethyl)piperazine sulfate which is still moist with, for example, methanol into a mixture of from about 0.7 to about 1 part by weight of methanol per part by weight of N-(2-sulfatoethyl)piperazine sulfate, deducting the parts by weight of methanol which are still in the methanol-moist N-(2-sulfatoethyl)piperazine sulfate, and from about 0.5 to about 0.7 part by weight of water, including the water which may have been introduced into the reaction mixture if the alkaline compound was in aqueous solution, or to transfer the N-(2-sulfatoethyl)piperazine sulfate which is still moist with, for example, ethanol into a mixture of from about 1.0 to about 1.3 parts by weight of ethanol per part by weight of N-(2-sulfatoethyl)piperazine sulfate, deducting the parts by weight of ethanol which are still in the ethanol-moist N-(2-sulfatoethyl)piperazine sulfate, and from about 0.4 to about 0.7 part by weight of water, including the water which may have been introduced into the reaction mixture if the alkaline compound was in aqueous solution.

The basic compound which is employed may be, for example, an alkali metalhydroxide, hydrogen carbonate, carbonate, methanolate and/or ethanolate, or a substance which forms, in the reaction medium, one of these compounds. It is preferred to employ the hydroxide, hydrogen carbonate, carbonate, methanolate and/or ethanolate of sodium or of potassium, particularly preferably the sodium compounds such as, for example, sodium hydroxide. The basic compounds can be employed as they are or in the form of aqueous solutions. Since the basic compounds employed with particular preference are the sodium compounds, the sulfate obtained in the process according to the invention is predominantly that of sodium, and is separated off.

The base is expediently employed in approximately twice the stoichiometric amount based on the N-(2-sulfatoethyl)piperazine sulfate; specifically, its amount is such as to bring about a pH of from about 6.0 to about 7.8, preferably from about 6.2 to about 7.5 and particularly preferably from about 6.7 to about 7.1.

For the isolation of the N-(2-sulfatoethyl)piperazine, from about 1.4 to about 2.6 parts by weight of alcohol per part by weight of N-(2-sulfatoethyl)piperazine sulfate employed are added to the filtrate obtained after separating off the sulfate of the base employed, for example sodium sulfate.

N-(2-Sulfatoethyl)piperazine is obtained in this manner in yields of ≧84% and in purities of ≧95%. N-(2-Sulfatoethyl)piperazine is obtained, in contrast to the prior art (see above) (viscous oil), as a crystalline powder with a decomposition point at 232° C.

The sulfuric-acid containing alcohol which is obtained in the course of the sulfonation (esterification) can be recovered by redistillation in vacuo and used again. The alcoholic mother liquors from the liberation of the N-(2-sulfatoethyl)piperazine from its salt can be used again without further purification. This enables a distinct reduction in the quantities of waste.

It is to be considered surprising that, with the temperatures and alcohol/water mixtures employed in accordance with the invention, it is possible simply and thoroughly to separate N-(2-sulfatoethyl)piperazine from alkali metal sulfate, preferably sodium sulfate.

The examples below are intended to illustrate the process according to the invention, without limiting it to them.

EXAMPLE 1

400.0 g of sulfuric acid (100% strength) are initially introduced into a 1 l four-necked flask fitted with stirrer, dropping funnel, thermometer and reflux condenser, and 260.4 g (2.0 mol) of N-(2-hydroxyethyl)piperazine are added over approximately 20 minutes at a rate such that the temperature does not exceed 150° C. 246.2 g of 65% strength oleum are then metered in, likewise at a rate such that 150° C. is not exceeded. The reaction mixture (906 g) is transferred to a dropping funnel, and approximately ⅓ of it is then metered into 890 g of ethanol (80% strength) at a rate such that the temperature does not exceed 45° C. The mixture is then cooled with stirring to about 20° C., seeded if desired with 0.1 g of N-(2-sulfatoethyl)piperazine sulfate, and stirred vigorously until the product crystallizes. Subsequently, the remainder of the reaction mixture is run in over 10 minutes at a rate such that the temperature does not exceed 30° C. The mixture is then cooled with stirring to 20° C. and the crystals are filtered off with suction. The product is washed with 900 g of ethanol (96% strength). 848 g of ethanol-moist N-(2-sulfatoethyl)piperazine sulfate are obtained.

339 g of water and 470.8 g of ethanol (96% strength) are initially introduced into a 2 l four-necked flask fitted with stirrer and internal thermometer, and 80.0 g (4.0 mol) of sodium hydroxide are added. After the solution has been cooled to 25° C., 848.2 g of ethanol-moist N-(2-sulfatoethyl)piperazine sulfate are added. The suspension is heated to 65° C. and stirred at this temperature for 30 minutes. The pH must be from 6.7 to 7.1 and is adjusted if necessary using sodium hydroxide solution or sulfuric acid. The precipitated sodium sulfate is then filtered off with suction. The filter cake is washed with 314 g of ethanol (96% strength) heated to 65° C. 320.4 g of ethanol-moist sodium sulfate are obtained. 813 g of ethanol and the wash liquor are added to the filtrate, and the precipitated product is filtered off with suction and washed with 300 g of ethanol (96% strength). The filter cake is dried at 70° C. and 100 mbar to give 380.3 g of N-(2-sulfatoethyl)piperazine as a white powder. The purity by titration is 95.5%, corresponding to 363.2 g (1.73 mol) of N-(2-sulfatoethyl)piperazine (calculated as 100% pure) and a yield of 86.4% of theory.

Melting point: 232° C. (decomposition, depending on the heating rate)

Calculated for $C_6H_{14}N_2O_4S$: C 34.3% H 6.6% N 13.3% S 15.2%

Found: C 33.2% H 6.5% N 12.9% S 14.9%

$^1$H-NMR ($D_6$DMSO): δ=2.58–2.67 (m; 6H; N($CH_2$)$_3$), 3.04–3.11 (m; 4H; HN($CH_2$)$_2$), 3.84 (t; 2H; $CH_2$—O), 8.2–8.6 (broad; 2H; NH, $OSO_3$H).

EXAMPLE 2

206.3 g of sulfuric acid (96% strength) are initially introduced into a 1 l four-necked flask fitted with stirrer, dropping funnel, thermometer, reflux condenser and gas inlet, and 130.2 g (1.0 mol) of N-(2-hydroxyethyl)piperazine are added over about 20 minutes with cooling, at a rate such that the temperature does not exceed 150° C. Then 169.9 g of chlorosulfonic acid are metered in over 1 hour with heating at 120° C. A vigorous stream of nitrogen is passed in throughout this procedure, because the reaction mixture foams (HCl evolution). After addition is complete, the mixture is subsequently stirred at 150° C. and while passing in nitrogen until no hydrogen chloride can be detected in the outgoing gas (about 1.5 hours). The reaction mixture (446.9 g) is transferred to a dropping funnel and then about ⅓ of it is metered into 447 g of ethanol (80% strength) at a rate such that the temperature does not exceed 45° C. Further reaction is then carried out as described in Example 1. The product is dried at 70° C. and 100 mbar to give 189.2 g of N-(2-sulfatoethyl)piperazine as a white powder. The purity by titration is 95.0%, corresponding to 179.7 g (0.86 mol) of N-(2-sulfatoethyl)piperazine (calculated as 100% strength) and a yield of 85.6% of theory.

Melting point: 237° C. (decomposition, depending on the rate of heating)

The spectroscopic and analytical data are identical to those given in Example 1.

EXAMPLE 3

200 g of sulfuric acid (100% strength) are initially introduced into a 1 l four-necked flask fitted with stirrer, dropping funnel, thermometer and reflux condenser, and 130.2 g (1.0 mol) of N-(2-hydroxyethyl)piperazine are added over about 20 minutes at a rate such that the temperature does not exceed 200° C. 123.1 g of oleum are then metered in over 1 hour at a rate such that the temperature does not exceed 200° C. The reaction mixture (453.2 g) is subsequently transferred to a dropping funnel, and then approximately ⅓ of it is metered into 453 g of methanol (80% strength) at a rate such that the temperature does not exceed 45° C. The mixture is then cooled with stirring to about 25° C., seeded if desired with 0.1 g of N-(2-sulfatoethyl)piperazine sulfate crystals, and stirred vigorously until the product crystallizes. Then the remainder of the reaction mixture is run in over 10 minutes at a rate such that the temperature does not exceed 25° C. The mixture is then stirred at 25° C. for 30 minutes and the crystals are filtered off with suction. The product is washed with 412 g of methanol. 394.2 g of methanol-moist N-(2-sulfatoethyl)piperazine sulfate are obtained.

186 g of water are initially introduced into 1 l four-necked flask fitted with stirrer and internal thermometer, and 80.0 g (2.0 mol) of sodium hydroxide are added. Subsequently, 172.3 g of methanol are metered in. 394.2 g of methanol-moist N-(2-sulfatoethyl)piperazine sulfate are added to this solution. The suspension is heated to 45° C. and stirred at this temperature for 30 minutes. The pH of the suspension must be from 6.7 to 7.1. The precipitated sodium sulfate is filtered off with suction. The filter cake is washed with 200 g of methanol heated to 45° C. 135.8 g of methanol-moist sodium sulfate are obtained. 370 g of methanol are added to the filtrate (mother liquor and methanol washings), which is then cooled to <5° C. and stirred at this temperature for 30 minutes, and the precipitated product is filtered off with suction. The filter cake is washed with 150 g of methanol. The filter cake is dried at 70° C. and 100 mbar to give 183.0 g of N-(2-sulfatoethyl)piperazine as a white powder. The purity by titration is 97.0%, corresponding to 177.5 g (0.84 mol) of N-(2-sulfatoethyl)piperazine (calculated as 100% pure) and a yield of 84.4% of theory.

Melting point: 237° C. (decomposition, depending on the rate of heating)

The spectroscopic and analytical data are identical with those given in Example 1.

EXAMPLE 4

(Comparative example in accordance with Tomalia et al., J. Heterocycl. Chem. 9, 891–894 (1972))

22.2 g (0.18 mol) of ethylene sulfate (for its preparation see Example 5) and 15.4 g (0.18 mol) of piperazine in 135 ml of methylene chloride are heated at reflux for 4 hours in a 500 ml four-necked flask fitted with stirrer, thermometer and reflux condenser. The reaction mixture was cooled to 5° C. The viscous, sticky mass which is deposited is separated off. 26.2 g of product are obtained after drying. Potentiometric titration and $^1$H-NMR analysis of the product reveal that it is not identical with N-(2-sulfatoethyl)piperazine.

EXAMPLE 5

(Comparative example in accordance with DE 10 49 870, Example 1)

46 g of ethylene sulfite are added to 23.4 ml of sulfuric acid monohydrate over 30 minutes at 23° C. When the evolution of gas has ended, the mixture is stirred for a further 30 minutes and, at room temperature, 128 ml of thionyl chloride are added with stirring. When the evolution of gas has ended, the mixture is heated to boiling for 15 hours. Subsequently, the excess thionyl chloride is distilled off, first at atmospheric pressure and then at 100 mbar. The residue is distilled at 15 mbar. 46.3 g of a dark brown distillate are obtained which is extracted with ether. 28.9 g of a beige powder are obtained (yield: 54.7% of theory).

We claim:

1. A process for the preparation of N-(2-sulfato-ethyl)piperazine in high purity, which comprises reacting N-(2-hydroxyethyl)piperazine in a mixture of about 0.8 to about 3 parts by weight of about 95 to 100% strength sulfuric acid per part by weight of N-(2-hydroxyethyl)piperazine and oleum or chlorosulfonic acid at temperatures of from about 80° to about 250° C., transferring the resulting sulfonation mixture to a water-miscible aliphatic alcohol at a temperature not to exceed 45° C., isolating the N-(2-sulfatoethyl)piperazine sulfate formed, treating the N-(2-sulfatoethyl)piperazine sulfate, still moist with alcohol, at temperatures of from about 35° to about 90° C. with a basic compound in a mixture of a ($C_1$–$C_2$)-alkanol and water, separating off the precipitated sulfate of the basic compound employed, and isolating the N-(2-sulfatoethyl)piperazine formed by the addition of methanol and/or ethanol wherein the resulting sulfonation mixture is from about 2.0 to about 6.0 parts by weight of methanol or ethanol per part by weight of N-(2-hydroxyethyl)piperazine.

2. The process as claimed in claim 1, wherein N-(2-hydroxyethyl)piperazine is reacted at temperatures of from about 100° to about 170° C.

3. The process as claimed in claim 1, wherein the N-(2-sulfatoethyl)piperazine sulfate, still moist with alcohol, is treated with the basic compound at temperatures of from about 40° to about 70° C.

4. The process as claimed in claim 1, wherein the basic compound is selected from the group consisting of an alkali metal hydroxide, hydrogen carbonate, carbonate, methanolate, ethanolate and a substance which forms, in the reaction medium, one of these compounds or mixtures thereof.

5. The process as claimed in claim 1, wherein the basic compound is selected from the group consisting of hydroxide, hydrogen carbonate, carbonate, methanolate, ethanolate of sodium, ethanolate of potassium or a substance with forms, in the reaction medium, one of these compounds and mixtures thereof.

6. The process as claimed in claim 1, wherein the reaction is carried out in from about 1.3 to about 1.7 parts by weight of 100% strength sulfuric acid per part by weight of N-(2-hydroxyethyl)piperazine.

7. The process as claimed in claim 1, wherein, when the reaction is carried out in a mixture of highly—or relatively highly—concentrated sulfuric acid and oleum, the content of sulfur trioxide in the oleum is from about 0.3 to about 0.8 part by weight per part by weight of N-(2-hydroxyethyl)piperazine.

8. The process as claimed in claim 1, wherein, when the reaction is carried out in a mixture of highly—or relatively highly—concentrated sulfuric acid and oleum, the content of sulfur trioxide in the oleum is from about 0.4 to about 0.7 part by weight per part by weight of N-(2-hydroxyethyl)piperazine.

9. The process as claimed in claim 1, wherein, when the reaction is carried out in a mixture of highly—or relatively highly—concentrated sulfuric acid and oleum, the content of sulfur trioxide in the oleum is from about 0.55 to about 0.65 part by weight per part by weight of N-(2-hydroxyethyl)piperazine.

10. The process as claimed in claim 1, wherein, when the reaction is carried out in a mixture of 100% strength sulfuric acid and chlorosulfonic acid, from about 0.6 to about 1.3 parts by weight of chlorosulfonic acid are employed per part by weight of N-(2-hydroxyethyl)piperazine.

11. The process as claimed in claim 1, wherein, when the reaction is carried out in a mixture of 100% strength sulfuric acid and chlorosulfonic acid, from about 0.7 to about 1.0 part by weight of chlorosulfonic acid is employed per part by weight of N-(2-hydroxyethyl)piperazine.

12. The process as claimed in claim 1, wherein, when the reaction is carried out in a mixture of 100% strength sulfuric acid and chlorosulfonic acid, from about 0.80 to about 0.95 part by weight of chlorosulfonic acid is employed per part by weight of N-(2-hydroxyethyl)piperazine.

13. The process as claimed in claim 1, wherein the resulting sulfonation mixture is transferred to from about 3.0 to about 5.0 parts by weight of methanol or ethanol per part by weight of N-(2-hydroxyethyl)piperazine.

14. The process as claimed in claim 1, wherein the resulting sulfonation mixture is transferred to from about 3.2 to about 3.8 parts by weight of methanol or ethanol per part by weight of N-(2-hydroxyethyl)piperazine.

15. The process as claimed in claim 1, wherein the resulting sulfonation mixture which is transferred to methanol or ethanol and wherein said methanol or ethanol has a water content of from about 10 to about 30% by weight.

16. The process as claimed in claim 1, wherein the resulting sulfonation mixture which is transferred to methanol or ethanol and wherein said methanol or ethanol has a water content of from about 15 to about 25% by weight.

17. The process as claimed in claim 1, wherein seed crystals of N-(2-sulfatoethyl)piperazine sulfate are added to the sulfonation mixture.

18. The process as claimed in claim 1, wherein the sulfuric acid-containing alcohol obtained after isolating the N-(2-sulfatoethyl)piperazine sulfate formed is recovered by distillation and used in a subsequent batch.

19. The process as claimed in claim 1, wherein the N-(2-sulfatoethyl)piperazine sulfate, still moist with methanol, is transferred into a mixture of from about 0.7 to about 1 part by weight of methanol per part by weight of N-(2-sulfatoethyl)piperazine sulfate, subtracted by the parts by weight of methanol which are still in the methanol-moist N-(2-sulfatoethyl)piperazine sulfate, and from about 0.5 to about 0.7 part by weight of water, including the water which may have been introduced into the reaction mixture if the alkaline compound was in aqueous solution.

20. The process as claimed in claim 1, wherein the N-(2-sulfatoethyl)piperazine sulfate, still moist with ethanol, is transferred into a mixture of from about 1.0 to about 1.3 parts by weight of ethanol per part by weight of N-(2-sulfatoethyl)piperazine sulfate, subtracted by the parts by weight of ethanol which are still in the ethanol-moist N-(2-sulfatoethyl)piperazine sulfate, and from about 0.4 to about 0.7 part by weight of water, including the water which may have been introduced into the reaction mixture if the alkaline compound was in aqueous solution.

21. The process as claimed in claim 1, wherein from about 1.4 to about 2.6 parts by weight of methanol and/or ethanol per part by weight of N-(2-sulfatoethyl)piperazine sulfate employed are added to the filtrate obtained after separating off the sulfate of the alkaline compound employed.

22. The process as claimed in claim 1, wherein the alcoholic mother liquors obtained in the course of liberation of the N-(2-sulfatoethyl)piperazine using the basic compound are used again without further purification.

23. The process as claimed in claim 1, which consists essentially of reacting N-(2-hydroxyethyl)piperazine in a mixture of about 0.8 to about 3 parts by weight of about 95 to 100% strength sulfuric acid per part by weight of N-(2-hydroxyethyl)piperazine and oleum or chlorosulfonic acid at temperatures of from about 80° to about 250° C., transferring the resulting sulfonation mixture to about 2.0 to about 6.0 parts by weight of methanol or ethanol per part by weight of N-(2-hydroxyethyl)piperazine at a temperature not to exceed 45° C., isolating the N-(2-sulfatoethyl)piperazine sulfate formed, treating the N-(2-sulfatoethyl)piperazine sulfate, still moist with alcohol, at temperatures of from about 35° to about 90° C. with a basic compound in a mixture of a $(C_1-C_2)$-alkanol and water, separating off the precipitated sulfate of the basic compound employed, and isolating the N-(2-sulfatoethyl)piperazine formed by the addition of methanol and/or ethanol.

24. The process as claimed in claim 1, which consists of reacting N-(2-hydroxyethyl)piperazine in a mixture of about 0.8 to about 3 parts by weight of about 95 to 100% strength sulfuric acid per part by weight of N-(2-hydroxyethyl)piperazine and oleum or chlorosulfonic acid at temperatures of from about 80° to about 250° C., transferring the resulting sulfonation mixture to a water-miscible aliphatic alcohol at a temperature not to exceed 45° C., isolating the N-(2-sulfatoethyl)piperazine sulfate formed, treating the N-(2-sulfatoethyl)piperazine sulfate, still moist with alcohol, at temperatures of from about 35° to about 90° C. with a basic compound in a mixture of a $(C_1-C_2)$-alkanol and water, separating off the precipitated sulfate of the basic compound employed, and isolating the N-(2-sulfatoethyl)piperazine formed by the addition of methanol and/or ethanol wherein the resulting sulfonation mixture is from about 2.0 to about 6.0 parts by weight of methanol or ethanol per part by weight of N-(2-hydroxyethyl)piperazine.

\* \* \* \* \*